United States Patent
Alreemi et al.

(10) Patent No.: US 12,285,418 B1
(45) Date of Patent: Apr. 29, 2025

(54) 2-(5-AMINOPYRIDIN-2-YL)-N-BENZYLACETAMIDES AND USE THEREOF IN THE TREATMENT OF ACUTE MYELOID LEUKEMIA

(71) Applicant: University of Jeddah, Jeddah (SA)

(72) Inventors: Roaa M. Alreemi, Jeddah (SA); Hind A. Alkhatabi, Jeddah (SA); Abdelsattar M. Omar, Jeddah (SA); Mohammed A. Baradwan, Jeddah (SA); Yosra A. Muhammad, Jeddah (SA); Peter Natesan Pushparaj, Jeddah (SA); Mohammad Basabrain, Jeddah (SA); Moustafa E. El-Araby, Richmond, VA (US)

(73) Assignees: University of Jeddah, Jeddah (SA); King Abdulaziz University, Jeddah (SA)

( * ) Notice: Subject to any disclaimer, the term of this patent is extended or adjusted under 35 U.S.C. 154(b) by 0 days.

(21) Appl. No.: 18/818,926

(22) Filed: Aug. 29, 2024

(51) Int. Cl.
*A61K 31/444* (2006.01)
*A61K 31/443* (2006.01)
*A61P 35/02* (2006.01)

(52) U.S. Cl.
CPC .......... *A61K 31/444* (2013.01); *A61K 31/443* (2013.01); *A61P 35/02* (2018.01)

(58) Field of Classification Search
CPC ...... A61K 31/443; A61K 31/444; A61P 35/02
See application file for complete search history.

(56) References Cited

U.S. PATENT DOCUMENTS 11,479,536 B1 * 10/2022 Omar .................. A61K 31/166

* cited by examiner

*Primary Examiner* — Shobha Kantamneni
(74) *Attorney, Agent, or Firm* — WCF IP

(57) ABSTRACT

Three compounds having a common molecular template of 2-(5-(N-acylamino)pyridin-2-yl)-N-benzylacetamide (Compounds I, II and I) are identified as potential anticancer therapeutic agents, and for the treatment of Acute Myeloid Leukemia (AML) in particular. Compound I was specifically designed to target AML cells, inhibit growth, and induce cell death. Compound I demonstrated a dose-dependent effect on AML cell lines HL-60, Mv4-11, KG-1a, and K562.

4 Claims, 18 Drawing Sheets

| Compound | HL60 | MV4-11 | KG1a | K562 |
|---|---|---|---|---|
| Compound I | 1.40 ± 0.5 | 1.46 ± 0.5 | 4.46 ± 0.6 | 4.73 ± 1.0 |
| Compound II | >10 | >10 | >10 | >10 |
| Compound III | >10 | >10 | >10 | >10 |

Fig. 6

| Gene Set | Description | Size | Expect | Ratio | P Value | FDR |
|---|---|---|---|---|---|---|
| hsa04110 | Cell cycle | 157 | 1.7981 | 9.4543 | 1.6345e-12 | 5.7536e-10 |
| hsa04068 | FoxO signaling pathway | 131 | 1.5003 | 9.9977 | 1.6644e-11 | 1.9529e-9 |
| hsa04218 | Cellular senescence | 156 | 1.7867 | 8.3955 | 2.0821e-10 | 1.8323e-8 |
| hsa05215 | Prostate cancer | 97 | 1.1109 | 9.9015 | 1.1145e-8 | 4.9039e-7 |
| hsa05200 | Pathways in cancer | 531 | 6.0816 | 3.7819 | 1.9933e-8 | 7.0163e-7 |
| hsa05223 | Non-small cell lung cancer | 72 | 0.82462 | 9.7015 | 0.0000014567 | 0.000039442 |
| hsa04115 | p53 signaling pathway | 74 | 0.84752 | 9.4393 | 0.0000018001 | 0.000042243 |
| hsa04668 | TNF signaling pathway | 114 | 1.3056 | 6.8931 | 0.0000056401 | 0.00011030 |
| hsa04670 | Leukocyte trans endothelial migration | 115 | 1.3171 | 6.8332 | 0.0000060616 | 0.00011230 |
| hsa04151 | PI3K-Akt signaling pathway | 359 | 4.1116 | 3.6482 | 0.000012577 | 0.00020122 |
| hsa05212 | Pancreatic cancer | 76 | 0.87043 | 8.0420 | 0.000023927 | 0.00033689 |

Fig. 10

| Molec. Parameter | Compound I |
|---|---|
| Formula | $C_{20}H_{18}N_4O_2$ |
| MW | 346.38 |
| #Heavy atoms | 26 |
| #Aromatic heavy atoms | 18 |
| Fraction Csp3 | 0.1 |
| #Rotatable bonds | 8 |
| #H-bond acceptors | 4 |
| #H-bond donors | 2 |
| MR | 98.31 |
| TPSA | 83.98 |
| iLOGP | 2.14 |
| XLOGP3 | 1.36 |
| WLOGP | 2.25 |
| MLOGP | 1.06 |
| Silicos-IT Log P | 2.96 |
| Consensus Log P | 1.95 |
| ESOL Log S | -2.83 |
| ESOL Solubility (g/l) | 0.514 |
| ESOL Class | Soluble |
| Ali Log S | -2.73 |
| Ali Solubility (g/l) | 0.651 |
| Ali Class | Soluble |

Fig. 17

| Druggability Parameter | Compound I |
| --- | --- |
| GI absorption | High |
| BBB permeant | No |
| Pgp substrate | Yes |
| CYP1A2 inhibitor | Yes |
| CYP2C19 inhibitor | Yes |
| CYP2C9 inhibitor | Yes |
| CYP2D6 inhibitor | Yes |
| CYP3A4 inhibitor | Yes |
| log Kp (cm/s) | -7.45 |
| Lipinski #violations | 0 |
| Ghose #violations | 0 |
| Veber #violations | 0 |
| Egan #violations | 0 |
| Muegge #violations | 0 |
| Bioavailability Score | 0.55 |
| PAINS #alerts | 0 |
| Brenk #alerts | 0 |
| Leadlikeness #violations | 1 |
| Synthetic Accessibility | 2.58 |

Fig. 18

2-(5-AMINOPYRIDIN-2-YL)-N-BENZYLACETAMIDES AND USE THEREOF IN THE TREATMENT OF ACUTE MYELOID LEUKEMIA

FIELD OF THE INVENTION

This invention pertains to the fields of pharmaceutical chemistry and oncology. Specifically, it is related to the development of novel compounds, namely, substituted amino 2-aryl-N-benzylacetamides. These compounds have demonstrated significant therapeutic potential in the treatment of Acute Myeloid Leukemia (AML), a type of cancer characterized by the rapid growth of abnormal white blood cells that accumulate in the bone marrow and interfere with normal blood cell production.

BACKGROUND

Acute Myeloid Leukemia (AML) is a severe and rapidly progressing form of leukemia characterized by the overproduction of immature white blood cells in the bone, which can interfere with the production of normal blood cells (Vakiti et al., 2024). Despite advances in the understanding of the genetic and molecular underpinnings of AML, treatment options have remained relatively unchanged for decades, often relying on a combination of cytarabine and anthracycline (DiNardo and Cortes, 2014; Medinger et al., 2019). The heterogeneity of AML, with its various cytogenetic and molecular abnormalities, presents a challenge for treatment as these factors significantly influence prognosis and response to therapy (Medinger et al., 2019). The development of novel synthetic compounds for the treatment of AML is of paramount importance due to several factors. First, current standard treatments do not lead to durable remission in the majority of patients, highlighting the need for more effective therapies (Dinardo and Cortes, 2014). Second, therapy-related AML, which can arise following treatment with cytotoxic agents for other malignancies, often has a poor prognosis and may respond differently to standard AML treatments (Koklu et al., 2015). Additionally, the complexity of AML pathophysiology, including its reliance on angiogenesis, suggests that targeting multiple pathways is necessary to improve the outcomes (Haouas, 2013). In conclusion, the development of novel synthetic compounds is critical for improving therapeutic outcomes for AML patients with AML. Such compounds could offer targeted treatment options, potentially overcoming the limitations of current therapies and addressing the diverse genetic landscape of AML (DiNardo and Cortes 2014). The importance of this research direction is underscored by its potential to provide individualized and more effective treatment strategies, ultimately leading to better prognosis and quality of life for patients with this aggressive disease (DiNardo and Cortes, 2014; Alkhatabi et al., 2022).

SUMMARY

Acute Myeloid Leukemia (AML) is an aggressive and heterogeneous blood cancer with high mortality rate and limited effective treatment options. Despite advancements in the understanding of the genetic and molecular mechanisms underlying AML, treatment regimens have remained largely unchanged over the past few decades. Standard AML treatments typically involve a combination of cytarabine and anthracyclines, which, while initially effective, often do not result in durable remission in most patients. This underscores the urgent need for new therapeutic strategies and agents that can effectively target diverse subtypes of AML.

The genetic and molecular heterogeneity of AML, characterized by various cytogenetic and molecular abnormalities, significantly influences prognosis and response to therapy. This diversity presents substantial challenges in the development of universally effective treatments. Current therapies often fail to address the specific needs of the different AML subtypes, leading to suboptimal patient outcomes.

In recent years, research has been increasingly focused on developing novel synthetic compounds that can potentially target AML cells more precisely.

Compounds I, II, and III, presented below, are novel substituted amino 2-aryl-N-benzylacetamide. In vitro studies have demonstrated that these compounds exhibit potent anti-leukemic activity in various AML cell lines, including HL-60, Mv4-11, KG-1a, and K562. These studies have shown that Compound I can effectively inhibit cell growth and induce cell death in a dose-dependent manner.

The development of compound I (MCP-324) as a therapeutic agent for AML represents significant advancement in AML treatment. The ability of the compound to selectively target AML cells over colon cancer cells and its ability to induce apoptosis offers a potential pathway for overcoming the limitations of existing therapies. Furthermore, the unique properties and mechanisms of action of Compound I could provide a valuable addition to the arsenal of AML treatment, potentially improving patient prognosis and quality of life.

In one aspect, the invention pertains to Compounds I, II and III, with the following structures:

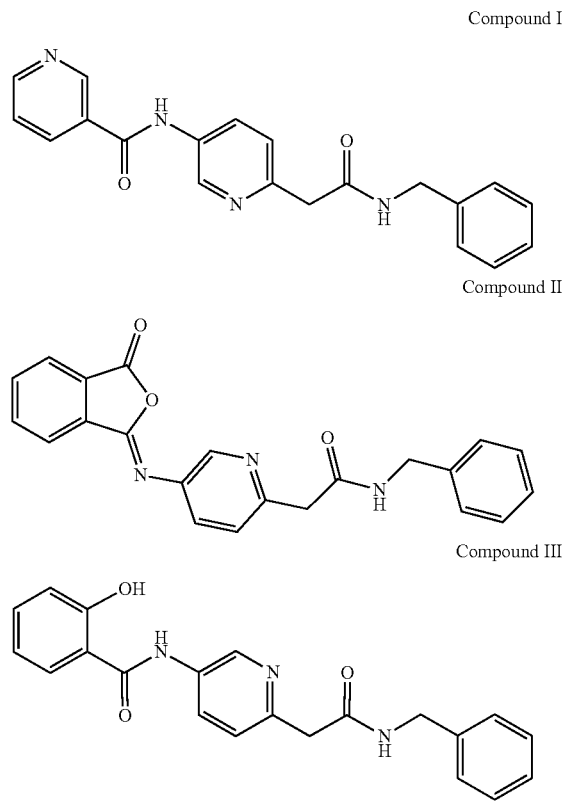

Compound I exhibited substantial effects on distinct AML cell lines. This compound has been tested at various concentrations ranging from 1 µM to 8 µM and has demonstrated dose-dependent effects on cell viability. These findings indicated that Compound I may have therapeutic potential for specific ailments or conditions. Compound I was meticulously synthesized and characterized using extensive laboratory experiments. The compound was examined in the HL-60, Mv4-11, KG-1a, and K562 cell lines, which represent various disease models and cell types of interest. The cell viability results obtained from these experiments indicated the therapeutic effects of Compound I. Comprehensive information regarding the synthesis and characterization of Compound I, as well as the experimental techniques used to assess its effects on cell lines. Compounds II and III exhibited weaker activity than Compound I in the above tests, but represent potential candidates for the same applications as Compound I.

Compounds I, II, and III are promising candidates as novel substituted amino 2-aryl-N-benzylacetamide. In vitro studies have demonstrated that these compounds exhibit potent anti-leukemic activity in various AML cell lines, including HL-60, Mv4-11, KG-1a, and K562. These studies have shown that Compound I can effectively inhibit cell growth and induce cell death in a dose-dependent manner.

The development of compound I (MCP-324) as a therapeutic agent for AML represents significant advancement in AML treatment. The ability of the compound to selectively target AML cells over colon cancer cells and its ability to induce apoptosis offers a potential pathway for overcoming the limitations of existing therapies. Furthermore, the unique properties and mechanisms of action of Compound I could provide a valuable addition to the arsenal of AML treatment, potentially improving patient prognosis and quality of life.

Recently, there has been increased interest in the discovery of innovative therapeutic agents that can effectively combat acute myeloid leukemia (AML) cells and improve patient outcomes (DiNardo et al., 2023). Compound I has shown great promise in preclinical studies, as it is a novel compound that has been specifically designed and synthesized to target AML cells and inhibit their growth or induce cell death. This compound was evaluated in various AML cell lines, including HL-60, Mv4-11, KG-1a, and K562, in order to assess its efficacy and potential as a therapeutic agent. This patent application introduced Compound I, a novel compound with potential applications in the treatment of AML. Compound I was specifically designed and synthesized to target AML cells, inhibit their growth, and induce cell death. This compound has demonstrated promising results in preclinical studies, showing dose-dependent effects on AML cell lines including HL-60, Mv4-11, KG-1a, and K562. The primary objective of this patent application was to secure intellectual property rights associated with Compound I and its specific application in the treatment of AML. By obtaining a patent, the inventor or assignee can establish exclusive rights to the compound, preventing others from using, manufacturing, or selling Compound I for AML treatment. This exclusivity provides a competitive advantage and opens opportunities for collaboration, licensing agreements, and commercialization.

Compound I may provide a targeted and effective treatment option for patients with AML, potentially improving their prognosis and quality of life. Furthermore, the unique properties and mechanisms of action of Compound I differentiate it from existing therapies, offering a valuable addition to the armamentarium of AML treatment. Below there is presented a detailed description of the synthesis and characterization of Compound I and the experimental procedures used to evaluate its effects on AML cell lines are provided. The results obtained from these experiments, including the dose-dependent effects on cell count percentages, are presented and analyzed. In addition, the potential applications and commercial advantages of Compound I in AML treatment are discussed.

DESCRIPTION OF THE DRAWINGS

FIG. 6. Table for cytotoxicity assays of Compound I, Compound II and Compound III Against Various Myeloid Leukemia Cell Lines expressed as $IC_{50} \pm SD$ (µM)
FIG. 7. Dose response curve of Compound I on myeloid leukemia cell lines. Cells were incubated with increasing concentration of compounds for 48 h and viability was assessed using an assay kit (in these studies, CellTiter®-Blue Cell Viability Assay kit was used).
FIG. 10. Table for KEGG pathways associated with cancer and inflammation impacted by Compound I based on WebGestalt analysis.
FIG. 17. Table for in silico molecular parameters of Compound I.

FIG. 18. Table for in silico drug pharmacokinetics and drug likeness parameters of Compound I.

DESCRIPTION OF THE INVENTION

Figure 1:
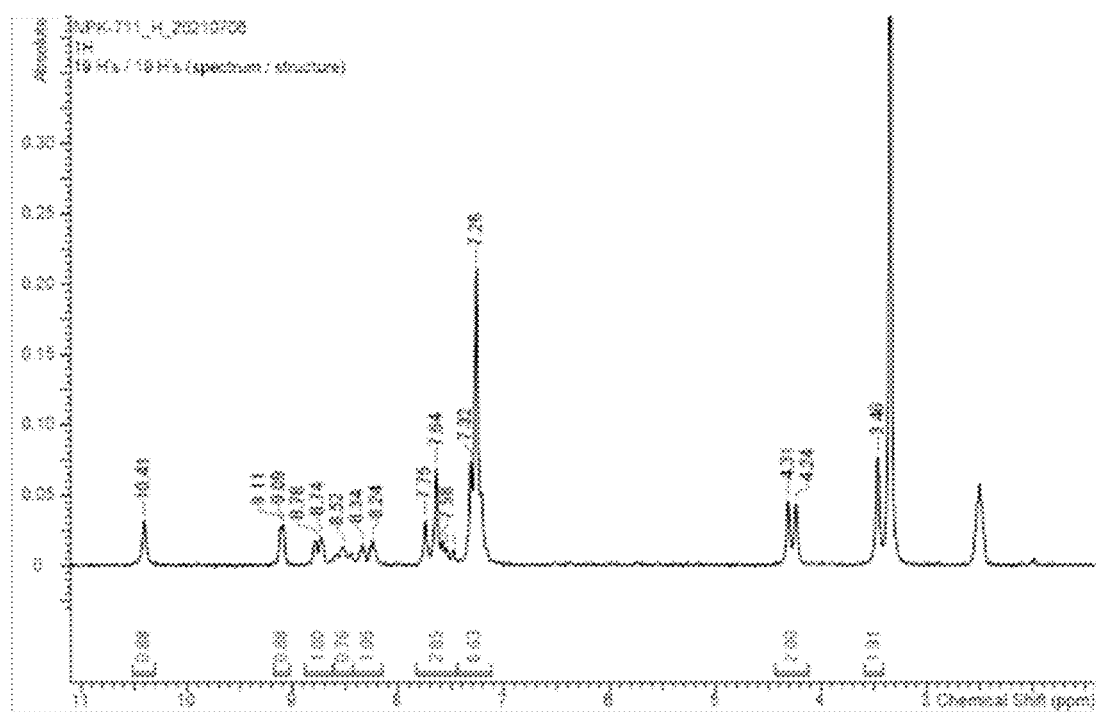
FIG. 1. 1H NMR spectrum of Compound I.
Figure 2:
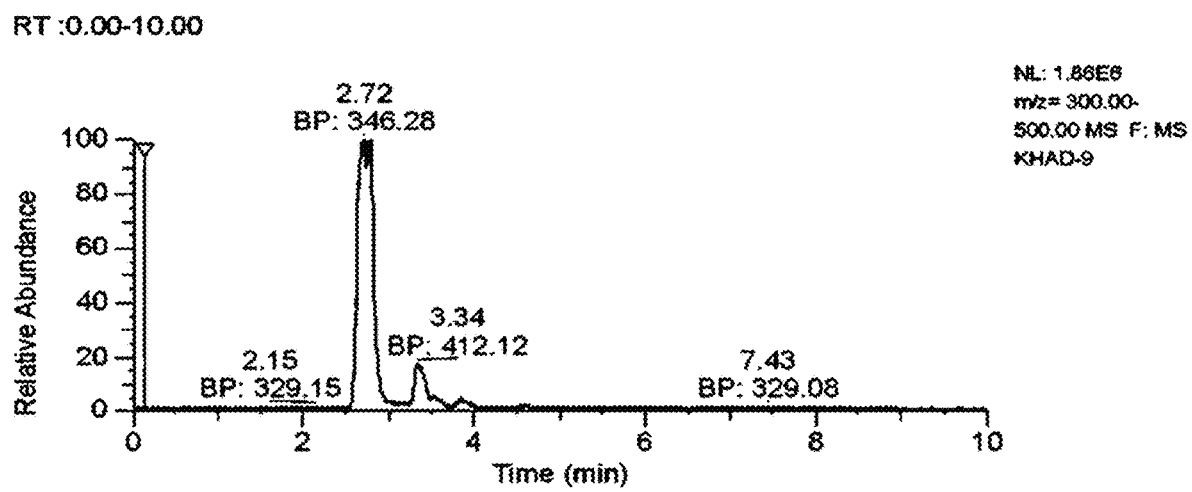
FIG. 2. LCMS spectrum of Compound I.
Figure 3:
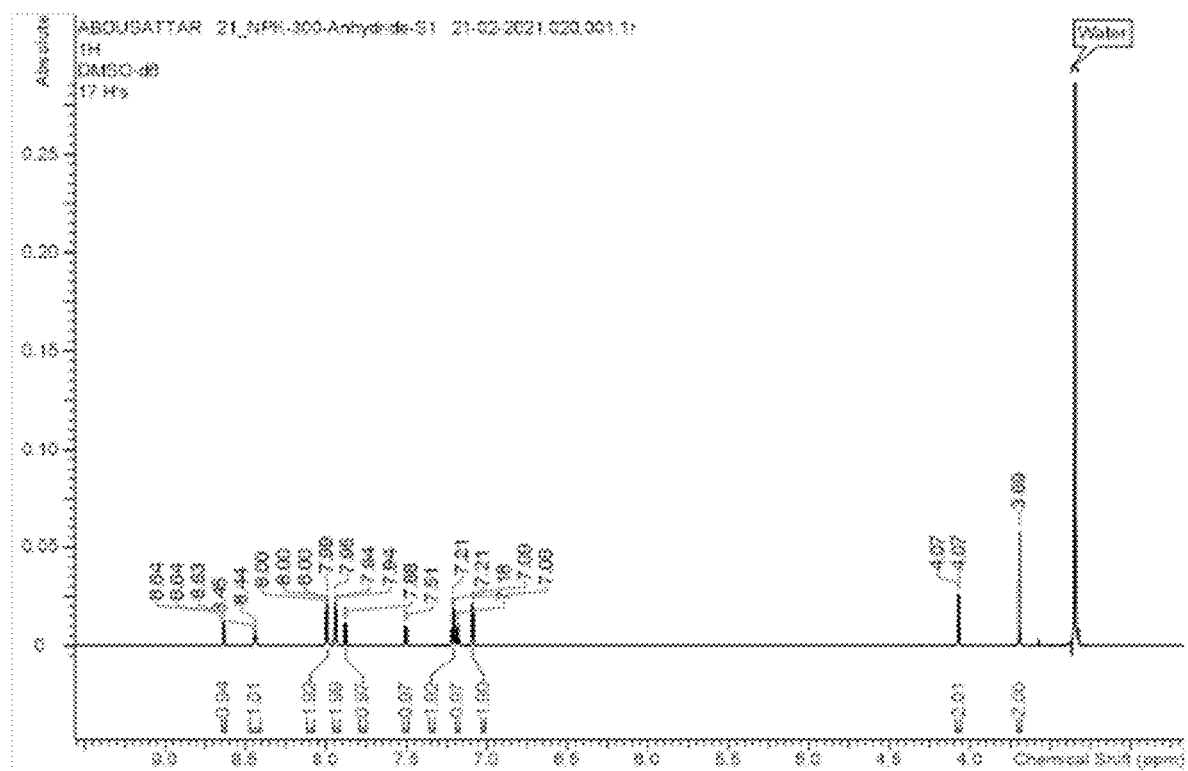
FIG. 3. 1H NMR spectrum of Compound II.
Figure 4:
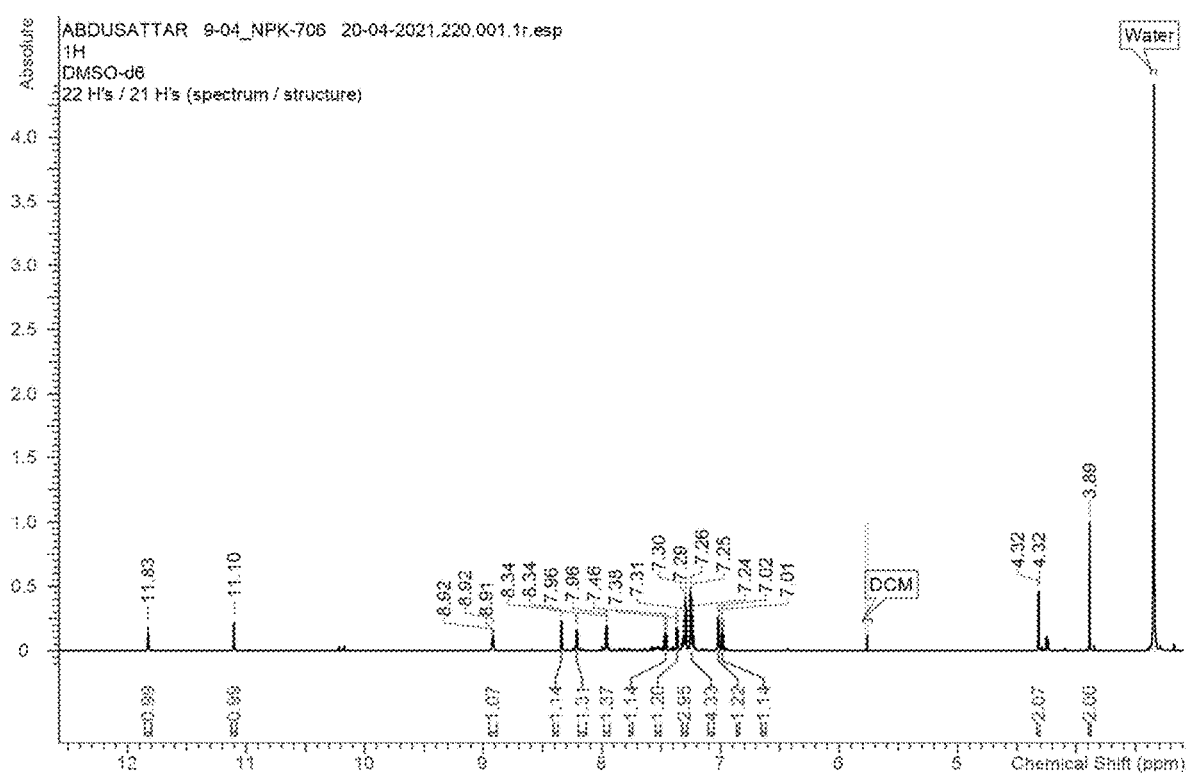
FIG. 4. 1H NMR spectrum of Compound III.
Figure 5:
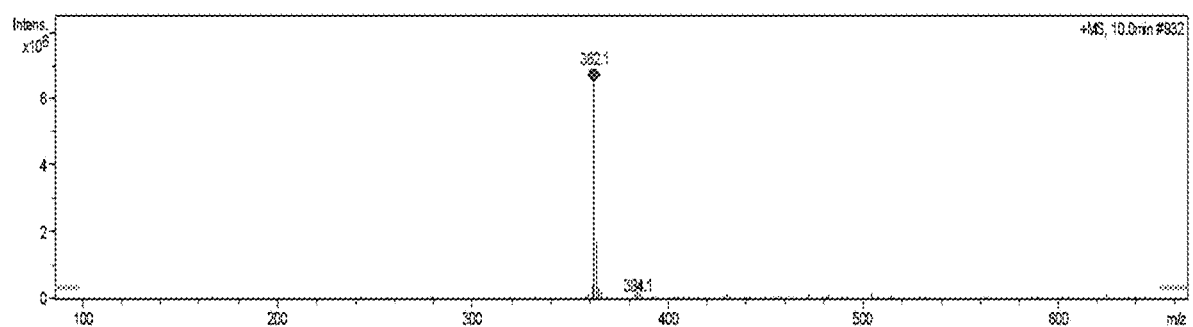
FIG. 5. LCMS spectrum of Compound III.

An aspect of the disclosure describes the synthesis and characterization of Compounds I, II and III which were designed to inhibit cancer cell signaling mechanisms and cancer cell proliferations. These compounds exhibited benefits in the treatment of oncogenic diseases.

In another aspect, Compound I demonstrated good potency in inhibiting the growth of AML cell lines and will be beneficial for treating leukemia.

In another embodiment, Compound I effectively increased the population of apoptotic cells in AML cell line models at $IC_{50}$ over control (untreated cells).

In a another aspect, the cytotoxic activities of Compound I were higher in leukemia cell lines than in the control (untreated cells) and colon cancer cell models (representing solid tumors).

In another embodiment, the tested cancer cell line models showed higher sensitivity to Compound I treatment than compounds II and III in AML cell lines.

In a related aspect of the invention, Compound I may target oncogenic pathways, such as cell cycle proteins, PI3K-AKT signaling, FoxO signaling, and TNF signaling. Compound I demonstrated convenient molecular parameters as a small-molecule drug candidate, high drug-likeness, and good pharmacokinetics in silico.

Methodology

Synthesis of N-(4-(2-(benzylamino)-2-oxoethyl) phenyl) nicotinamide (Compound I)

Nicotinic acid (0.5 g, 4.06 mmol), 2-(5-aminopyridin-2-yl)-N-benzylacetamide (1.1 eq), and HBTU (2 equiv) were added to a solution of N, N-diisopropylethylamine (3 eq) and DMF. The mixture was stirred at 80° C. for 45 min using a microwave. The mixture was added to ice water and washed with ethyl acetate. The organic layer was then washed with $NaHCO_3$, water, and brine. After evaporation, the crude product was purified by crystallization from ethyl acetate. The pure product (20.2%) had the following characterization profile: mp 206-207° C.; 1H NMR (80 MHz, DMSO-d6) δ 10.41 (s, 1H), 9.10 (d, 1H, J=1.7 Hz), 8.76 (d, 1H, J=3.5 Hz), 8.4-8.6 (m, 1H), 8.2-8.4 (m, 1H), 7.4-7.8 (m, 3H), 7.1-7.4 (m, 7H), 4.28 (d, 2H, J=6.0 Hz), 3.46 (s, 2H), LCMS, RT=2.75 min; m/z 346.28 [M+H]+.

Synthesis of (Z)-N-benzyl-2-(5-((3-oxoisobenzo-furan-1 (3H)-ylidene)amino)pyridin-2-yl) acetamide (Compound II)

Phthalic anhydride (2 mmol) was added to a solution of 2-(5-aminopyridin-2-yl)-N-benzylacetamide (2 mmol) in 1,2-dichloroethane (22 mL) was added phthalic anhydride (2 mmol), and the mixture was stirred at room temperature for 4 h. The resulting precipitate was filtered and washed with hexane to yield 2-((6-(2-(benzylamino)-2-oxoethyl) pyridin-3-yl) carbamoyl)benzoic acid as a beige solid (42% yield).

The acid was suspended in dry 1,4-dioxane, and a mixture of acetic anhydride (3 equiv) and triethylamine (6 eq) was added dropwise. After stirring overnight at RT, the reaction mixture was poured into ice and the solid precipitate was filtered and washed with sodium bicarbonate and water. The air-dried solid product yielded 58.2% beige solids with the following characterization profile: Mp: 161.7-163° C. 1H NMR (DMSO-$d_6$, 850 MHz) δ 8.63 (dd, 1H, J=1.6, 4.7 Hz), 8.44 (br t, 1H, J=5.7 Hz), 8.00 (dd, 2H, J=3.1, 5.4 Hz), 7.94 (dd, 2H, J=3.1, 5.4 Hz), 7.88 (dd, 1H, J=1.6, 7.8 Hz), 7.50 (dd, 1H, J=4.7, 7.8 Hz), 7.2-7.2 (m, 2H), 7.2-7.2 (m, 1H), 7.09 (d, 2H, J=7.3 Hz), 4.07 (d, 2H, J=5.7 Hz), 3.69 (s, 2H).

Synthesis of N-(6-(2-(Benzylamino)-2-oxoethyl) pyridin-3-yl)-2-hydroxybenzamide (Compound III)

2-hydroxybenzoic acid (0.1 g, 0.66 mmol) in THF was added slowly to a cooled solution of 2-(5-aminopyridin-2-yl)-N-benzylacetamide (1.2 eq) and TEA (3 eq). The reaction mixture was stirred at 0° C. for a few minutes and then left overnight at room temperature. After completion of the reaction, the solvent was evaporated and the product was extracted with EtOAc and washed with $NaHCO_3$. The crude product was purified on silica gel using flash chromatography (gradient 1:1 hexane/EtOAc). The pure product (13.7%) had the following characterization profile: mp 164-167° C.; 1H NMR (850 MHz, DMSO-$d_6$) δ 11.83 (s, 1H), 11.10 (s, 1H), 8.92 (t, 1H, J=6.0 Hz), 8.34 (dd, 1H, J=1.6, 4.7 Hz), 8.21 (d, 1H, J=8.3 Hz), 7.9-8.0 (m, 1H), 7.46 (t, 1H, J=7.5 Hz), 7.37 (dd, 1H, J=4.7, 8.0 Hz), 7.3-7.3 (m, 3H), 7.2-7.3 (m, 4H), 7.02 (d, 1H, J=9.0 Hz), 6.99 (t, 1H, J=7.2 Hz), 4.32 (d, 2H, J=6.0 Hz), 3.89 (s, 2H); 13C NMR (214 MHz, DMSO-$d_6$) δ 170.4, 166.6, 145.7, 139.4, 134.4, 133.7, 132.6, 129.8, 128.8, 127.7, 127.5, 127.3, 122.8, 119.8, 117.7, 42.8, 42.6; LCMS; RT=10.0 min; m/z 362.1 [M+H]+.

Biological Screening

Cell Viability Assay

Cell viability was determined using the CellTiter®-Blue Cell Viability Assay kit (Promega, Madison, WI, USA) as previously described (Alkhatabi et al., 2022). Approximately $10^4$ cells were counted, plated in a 96-well plate in the presence of test compounds ranging from 0.01 to 40 μM in quadruplicate, and incubated for 48 h at 37° C. in a humidified incubator. After the incubation period was completed, 20 μL of CellTiter®-Blue Cell Viability Assay reagent was added to each well and incubated for an additional 2 h for fluorescence development. Florescence was measured at Ex/Em 540/590 on a SpectraMax® i3 Multi-Mode microplate reader (Molecular Devices, LLC, San Jose, CA, USA) and plotted against the drug concentration to determine the IC50 of the test compounds. The IC50 was obtained by a nonlinear regression model using GraphPad Prism 10.1.1 (GraphPad Software, Inc., USA).

Apoptosis Assay

The annexin V-FITC and propidium iodide (PI) staining method was used to assess the effect of Compound I on leukemic cell lines using BDFACS Canto II clinical flow cytometry (BD Biosciences, USA), as previously described (Alkhatabi et al., 2022). Briefly, $1.5 \times 10^5$ cells were plated in a 6-well plate and harvested after 48 h of Compound I treatment. The collected cells were stained using the BD Annexin V FITC Apoptosis Detection Kit II, and the stained samples were analyzed by acquiring a minimum of 10,000 events at the gate; the emission wavelengths were 520 and 620 nm.

Cell Cycle Analysis

Cell cycle analysis was performed according to the manufacturer's protocol (P1304MP; Invitrogen). Approximately $3.5 \times 10^5$ cells were incubated with Compound I for 48 hrs at 37° C. The cells were collected and washed twice with (1×) PBS. Subsequently, the cells were fixed on ice for 20 min using 75% cold ethanol, stained with Thermo Fisher Propidium Iodide/RNase A, and processed using a BD FACS Canto II clinical flow cytometry system (BD Biosciences, USA). A minimum of 20,000 events were recorded at the gate and the emission wavelengths were 520 and 620 nm, respectively.

In Silico Analysis of Compound I Molecular Targets and Enriched Pathways

The top 100 molecular targets of Compound I were deduced using the SwissTargetPrediction tool. The molecular targets of Compound I were used to identify enriched pathways based on the Kyoto Encyclopedia of Genes and Genomes (KEGG) database using the over-representation analysis (ORA) method with the WebGestalt tool (Subramanian et al., 2007; Elizarraras et al., 2024).

Statistical Analysis

The half-maximal inhibitory concentration (IC50) of each drug was calculated using the GraphPad Prism software version 10.1.1. Flow cytometric data were analyzed using Diva software provided with the BD FACSCanto II Clinical Flow Cytometry System (BD Biosciences, USA). Student's paired t-test and Two-way ANOVA were used to compare data points. Data are presented as mean+SD, and at least three independent experiments were performed. Values of p less than 0.05 were regarded as statistically significant (*P≤0.05, P≤ 0.01, *P≤0.001, ****P≤0.0001).

Results

Synthesis: The structures of the compounds prepared according to the above methods were confirmed by spectral analyses (FIG. 1-5).

Figure 7:
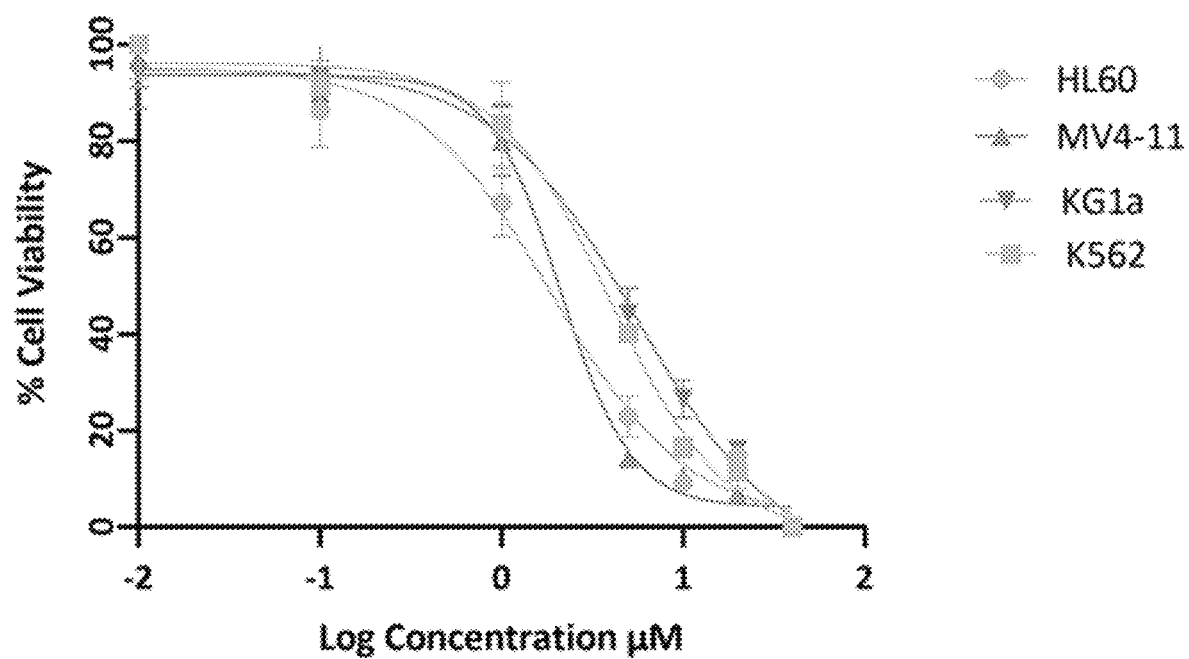

Cell Viability Assay: The Cell Viability Assay revealed that Compound I exhibited dose-dependent cytotoxicity, as evidenced by the decrease in cell viability with increasing concentrations of Compound I (FIG. 6). The dose-response curves (FIG. 7) illustrate that Compound I reduced the ratio of live cancer cells upon increasing the concentration of the compound. The $IC_{50}$ values obtained for Compound I against HL60, MV4-11, KG1a, and K562 cell lines were 1.40±0.5 µM, 1.46±0.5 µM, 4.46±0.6 µM, and 4.73±1.0 µM, respectively (FIG. 6). These findings suggest that Compound I has potent cytotoxic effects on myeloid leukemia cells, with HL60 and MV4-11 cells being more sensitive to the compound than KG1a and K562 cells. The lower IC50 values for HL60 and MV4-11 indicate that these cell lines require lower concentrations of Compound I to inhibit their growth by 50%. In contrast, KG1a and K562 cells exhibited higher $IC_{50}$ values, indicating that they were less sensitive to Compound I.

We also studied the cytotoxic effects of other related compounds, such as II and III, against myeloid leukemia cell lines (FIG. 6). The $IC_{50}$ values for compounds II and III were higher than 10 µM for all cell lines, indicating that these compounds were less effective in inhibiting cell growth than Compound I.

Figure 8:
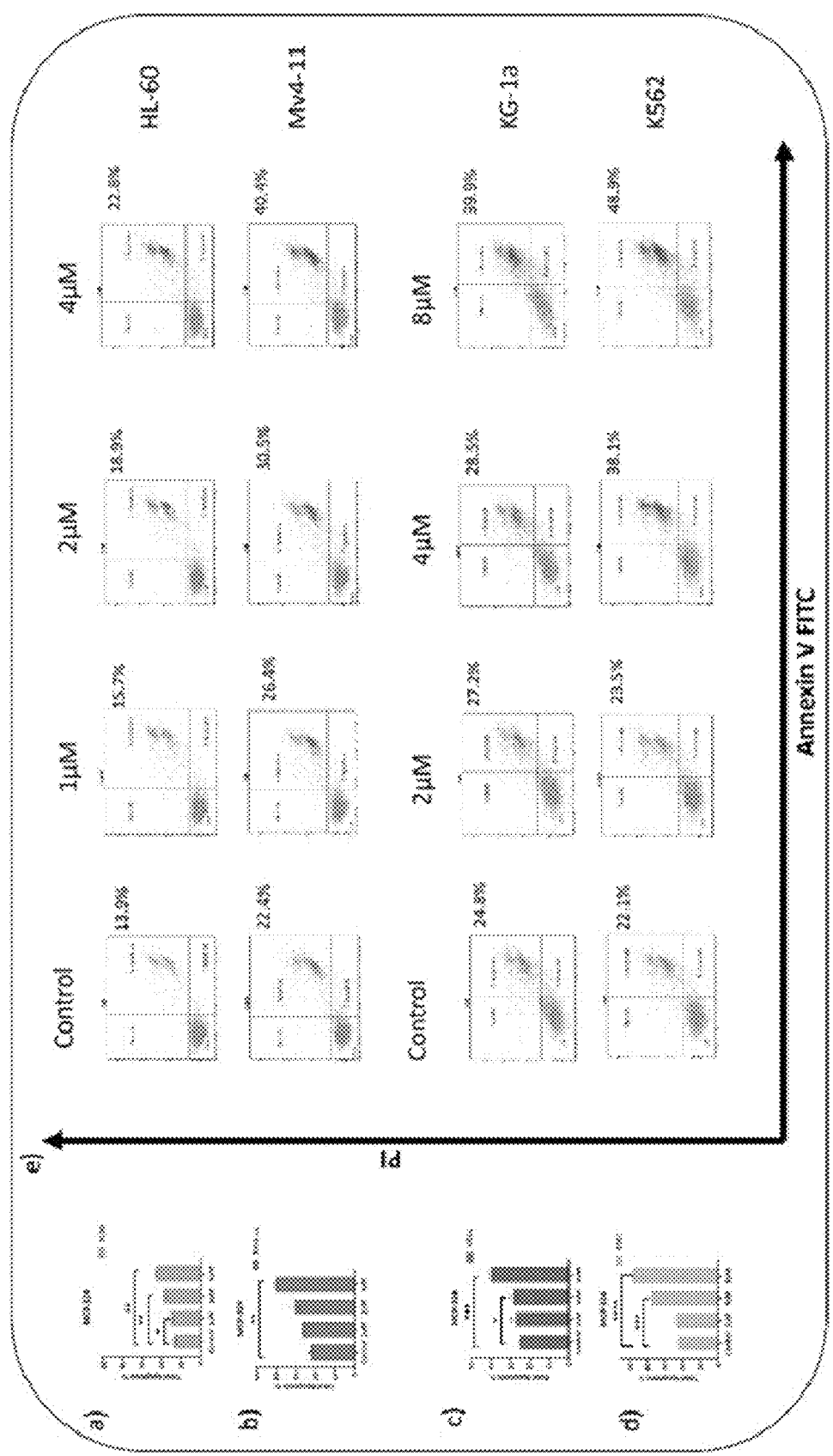
FIG. 8. Apoptosis assay based on the annexin V-FITC and propidium iodide (PI) staining method using Flow Cytometry. (a-d) The mean percentage of the total apoptotic cells with error bars representing SD. One-way ANOVA was performed to measure the significance. *$p<0.05$. (e) Representative scatter plots from flow cytometry for AML cells after they were exposed to the relevant MCP-324 doses for 48 hours and stained for an Annexin-V assay.

The apoptosis assay further supported the cytotoxic effects of Compound I on leukemic cell lines. Annexin V-FITC and propidium iodide staining revealed an increase in the number of apoptotic cells after treatment with Compound I (FIG. 8). This indicates that Compound I induces programmed cell death in leukemic cells, contributing to its cytotoxicity.

Figure 9:
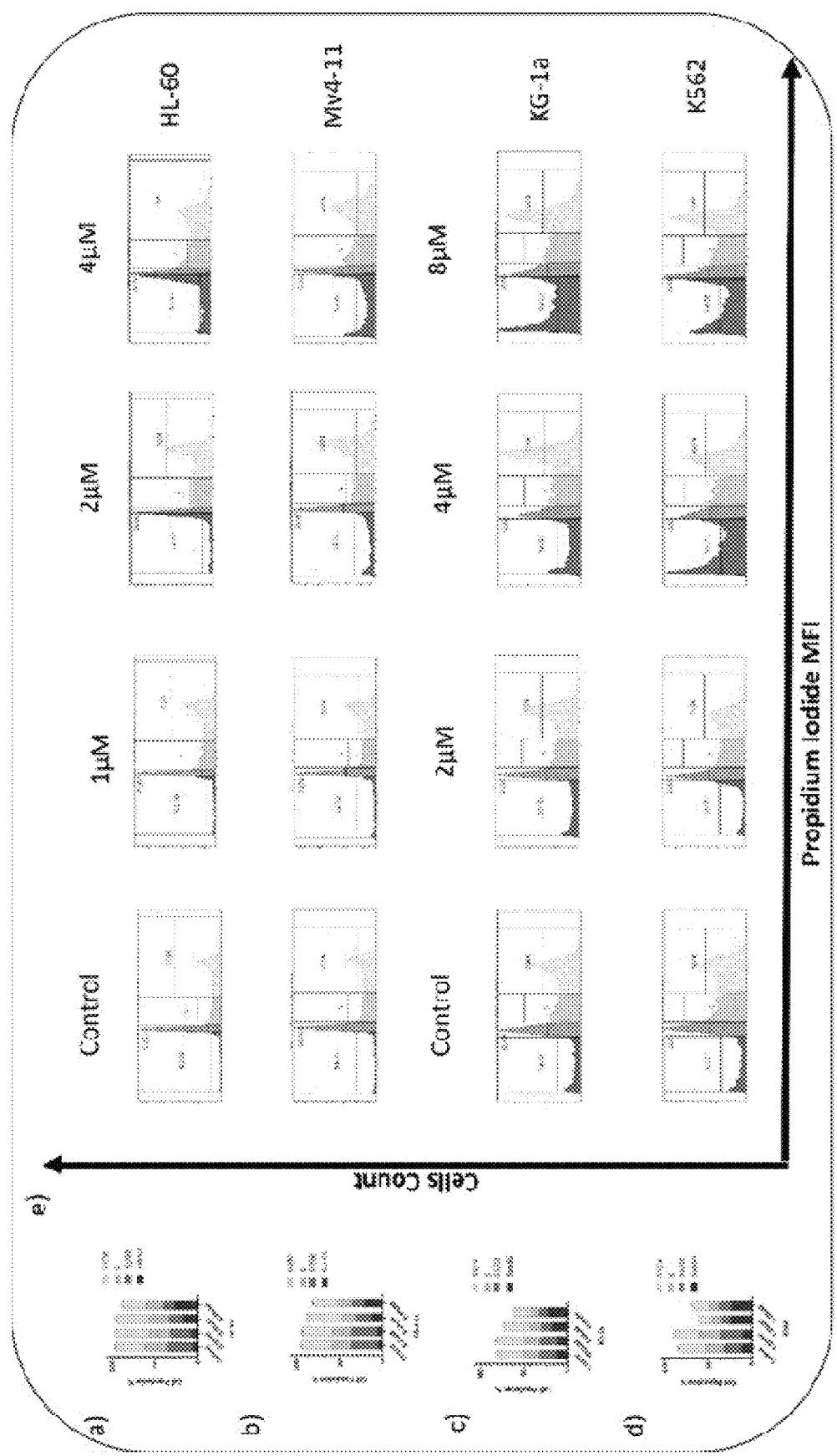
FIG. 9. Cell Cycle Analysis based on Propidium Iodide Staining Method using Flow Cytometry. (a-d) Representative bar graph of the percentage of cells in different stages of cell cycle as mean±SD. (e) The effect of MCP-324 in dose dependent manner on the four AML cell lines compared to untreated (control) cells for 48 hours.

Additionally, cell cycle analysis demonstrated that Compound I treatment resulted in alterations in the cell cycle distribution of leukemic cells. Compound I interferes with cell cycle progression, leading to cell cycle arrest at the sub $G_0$ (apoptotic) phase and subsequent cell death (FIG. 9).

Overall, the results demonstrate that Compound I as a promising therapeutic agent for myeloid leukemia. Its ability to induce cytotoxicity, apoptosis, and cell cycle arrest in leukemic cells suggests its potential as a targeted therapeutic agent. Further investigations are warranted to elucidate the underlying mechanisms of the cytotoxic effects of Compound I and to evaluate its efficacy and safety in preclinical and clinical settings.

In silico analysis showed that Compound I was likely involved in pathways involved in cell carcinogenesis. When in silico prediction methods were analyzed along with cell cycle effect results, certain cell signaling pathways were suggested to be targets of Compound I: Cell cycle signaling kinases, PI3K-AKT signaling, FoxO signaling, and TNF signaling. Compound I's potential as an inhibitor of signaling molecules within various Kyoto Encyclopedia of Genes and Genomes (KEGG) (Kanehisa and Goto 2000, Lu, Zhang et al. 2020) pathways relevant to cancer biology is a subject of importance in this patent application (www. https://www.genome.jp/kegg/). KEGG pathways, including those related to cancer, cell cycle, P53, PI3K-AKT, FoxO, and TNF signaling, represent a network of interactions that are critical for the regulation of cell proliferation, survival, and apoptosis. The inhibition of key molecules within these pathways could disrupt cancer cell growth and induce cell death, thus offering therapeutic potential. Interestingly, the PI3K-AKT pathway, which is central to many cellular functions, is negatively regulated by the FoxO transcription factors. The phosphorylation of FOXO by AKT results in its inactivation, which promotes cell survival and proliferation (Zhang et al., 2011). This suggests that by inhibiting AKT, Compound I could prevent FoxO phosphorylation, thereby activating its tumor-suppressive functions. Moreover, the PI3K-AKT pathway is involved in P53 tumor suppressor signaling, which is pivotal for cell cycle arrest and apoptosis (Liang et al., 2019). Inhibition of this pathway by Compound I could enhance P53 activity, leading to tumor suppression. Additionally, the TNF signaling pathway, which can induce inflammation and cancer progression, may also be modulated by Compound I, potentially reducing cancer cell viability. In summary, inhibition of signaling molecules within the KEGG pathways of cancer, cell cycle, P53, PI3K-AKT, FoxO, and TNF signaling by Compound I could have significant implications for cancer therapy. By targeting these pathways, Compound I may disrupt cancer cell growth and survival, promote apoptosis, and potentially offer a novel approach to cancer treatment.

We tested the effects of Compound I on different leukemia cell lines. The dose-response curve of Compound I in myeloid leukemia cell lines demonstrated its potential as a cytotoxic agent.

HL60: The $IC_{50}$ value for Compound I against HL60 cells was 1.40±0.5 µM. This suggests that HL60 cells are relatively sensitive to Compound I, as a lower concentration of the compound is needed to achieve 50% growth inhibition.

MV4-11: The $IC_{50}$ value for Compound I against MV4-11 cells was 1.46±0.5 µM. Similar to HL60 cells, MV4-11 cells also exhibited sensitivity to Compound I, which required a relatively low concentration for growth inhibition.

KG1a: The $IC_{50}$ value for Compound I against KG1a cells was 4.46±0.6 µM. This indicates that KG1a cells are less sensitive to Compound I than HL60 and MV4-11 cells, as a higher concentration of the compound is needed for growth inhibition.

K562: The $IC_{50}$ value for Compound I against K562 cells was 4.73±1.0 µM. Similar to KG1a cells, K562 cells also showed lower sensitivity to Compound I, requiring a higher concentration for growth inhibition.

These results indicate that Compound I exhibits varying cytotoxic effects on different myeloid leukemia cell lines. HL60 and MV4-11 cells appeared to be more sensitive to compound I, whereas KG1a and K562 cells exhibited relatively lower sensitivities. The differences in $IC_{50}$ values may be attributed to variations in the genetic and molecular characteristics of cell lines.

The inhibitory effect observed in MV4-11 and K562 cells at higher concentrations suggested that Compound I had a negative impact on the proliferation and survival of these cell lines. Future studies could explore the molecular pathways involved in these effects and investigate the potential therapeutic applications of Compound I for these specific cell types.

The results of the apoptosis assay using flow cytometry would provide valuable insights into the effect of Compound I on leukemic cell lines. By staining the cells with annexin V-FITC and propidium iodide (PI), it is possible to distinguish between viable, early apoptotic, late apoptotic, and necrotic cells. The results showed an increase in the percentage of cells in the early and late apoptotic quadrants compared to the control group, suggesting that Compound I has a pro-apoptotic effect on leukemic cells. This indicates that Compound I treatment may induce programmed cell death in leukemic cell lines, potentially through the activation of apoptotic pathways. These findings indicate that Compound I has the potential to be a therapeutic agent for myeloid leukemia by promoting apoptosis in leukemic cells. Cell cycle analysis using flow cytometry provided information on the distribution of cells in different phases of the cell cycle. By staining the cells with a DNA-binding dye, such as propidium iodide, it is possible to quantify the percentage of cells in the G0/G1, Sand G2/M phases of the cell cycle. Flow cytometry results showed an increase in the percentage of cells in the sub G1 phase compared to that in the control group, suggesting that Compound I affects cell cycle progression. This indicates that Compound I induces cell cycle arrest or alters cell cycle dynamics in leukemic cell lines and causes apoptosis in AML cells. These findings are significant, as dysregulation of the cell cycle is a hallmark of cancer and targeting cell cycle progression could be a potential therapeutic strategy for myeloid leukemia. Hence, the flow cytometry results from the apoptosis assay and cell cycle analysis provided valuable information regarding the effects of Compound I on leukemic cell lines. These results would contribute to our understanding of the mechanism of action of Compound I and its potential as a therapeutic agent for myeloid leukemia.

The dose-response curve provides a general overview of the cytotoxic effects of Compound I on myeloid leukemia cells. As indicated above, Compound I has cytotoxic effects on different AML cell lines. The observed variations in cytotoxicity suggested cell line-specific responses to Compound I.

Figure 11:
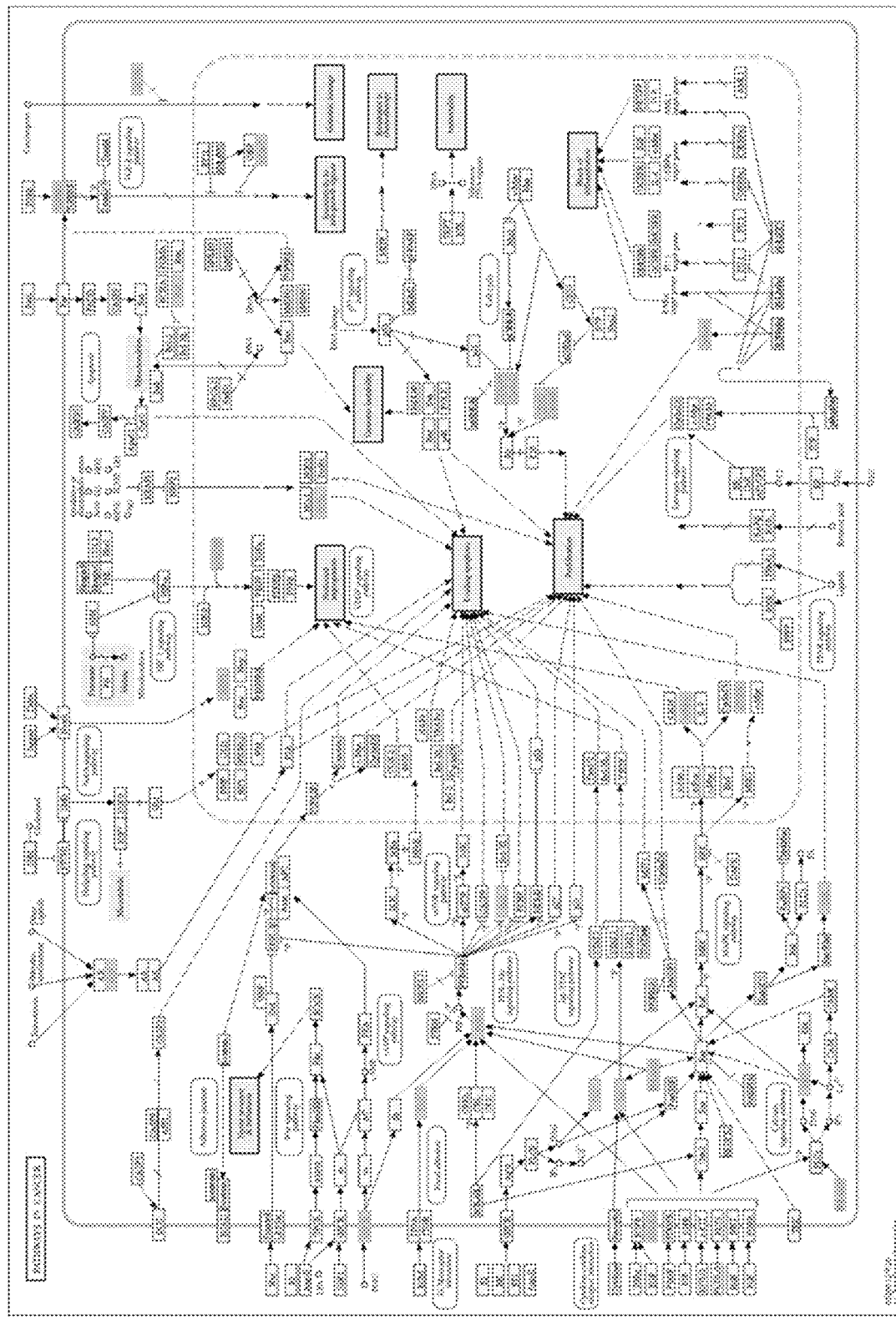
FIG. 11. Illustration of the pathways in cancer according to KEGG. The molecules that are involved in the cancer pathways targeted by Compound I are depicted in a grey color.
Figure 12:
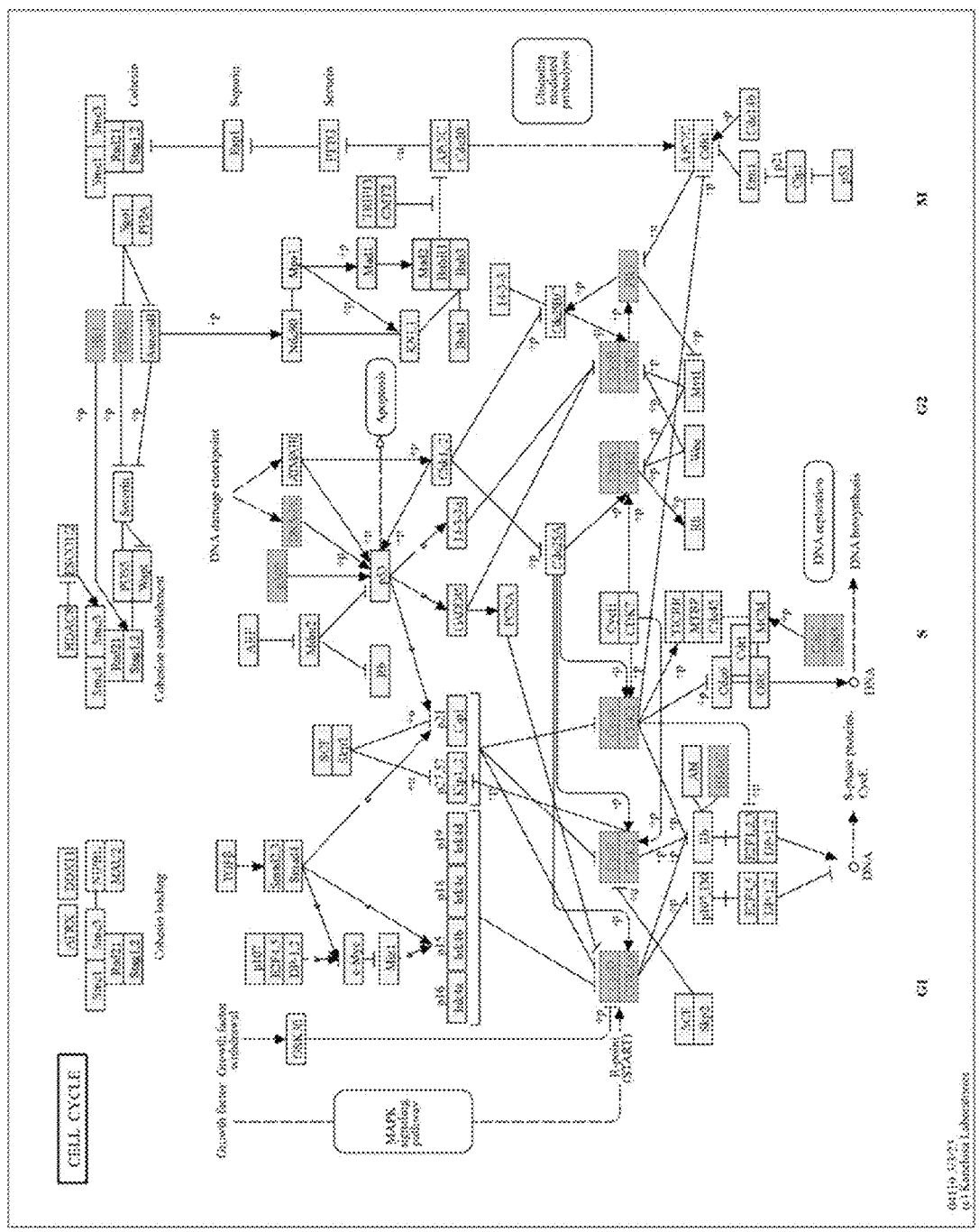
FIG. 12. Illustration of the pathways in cell cycle regulation according to KEGG. The molecules that are involved in cell cycle targeted by Compound I are depicted in a dark grey color.
Figure 13:
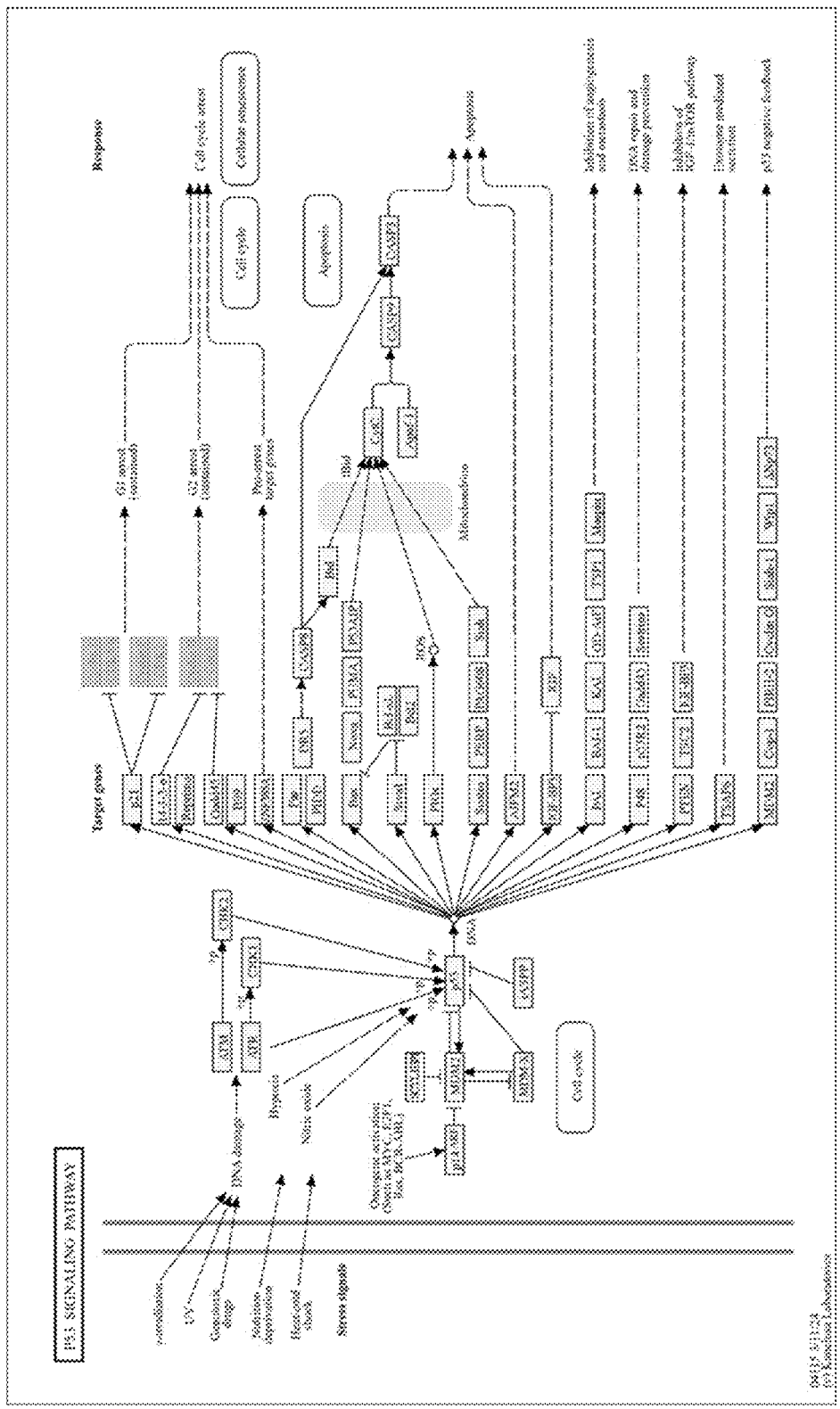
FIG. 13. Illustration of the pathways in P53 signaling according to KEGG. The molecules that are involved in the P53 signaling targeted by Compound I are depicted in a dark grey color.
Figure 14:
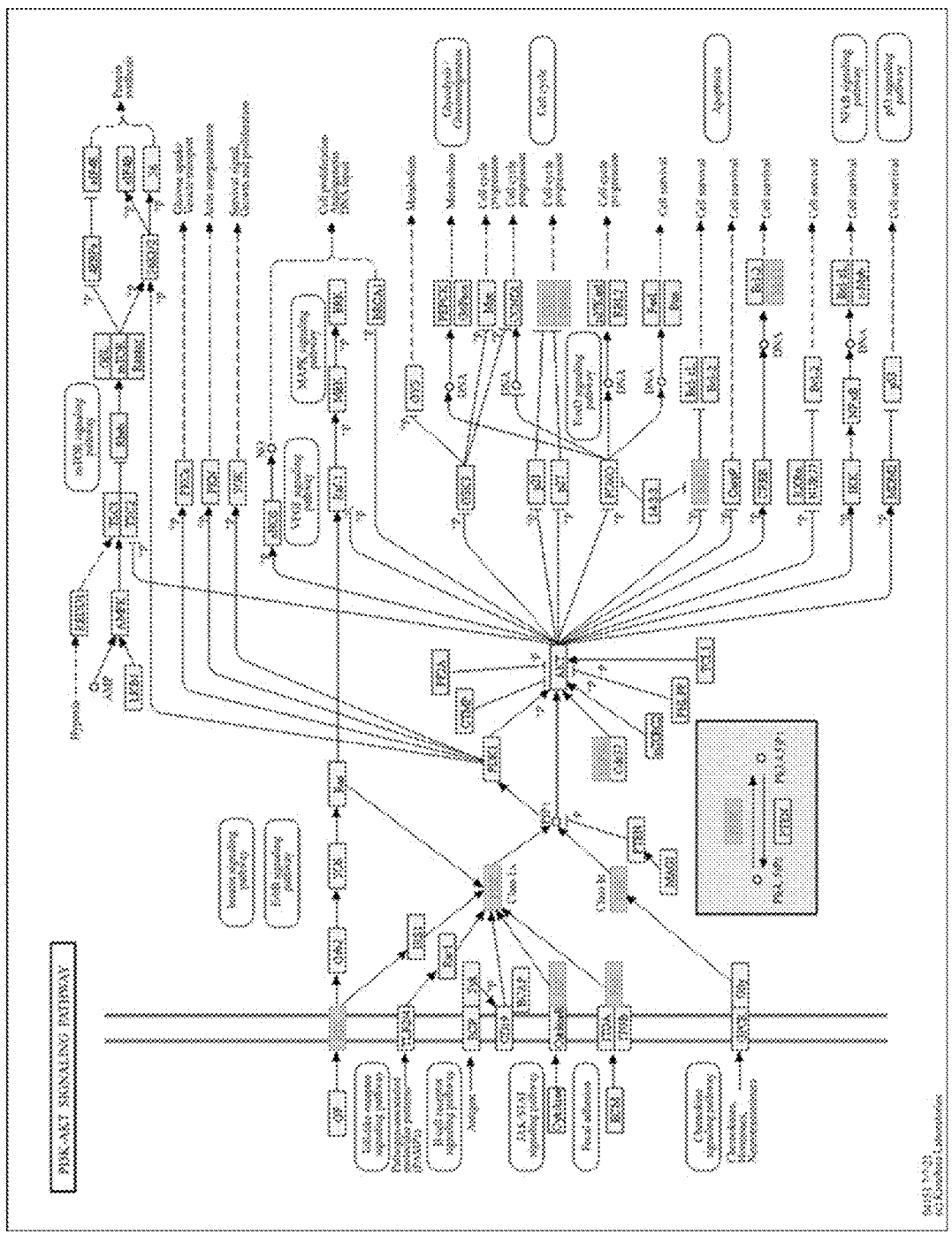
FIG. 14. Illustration of the pathways in PI3K-AKT signaling according to KEGG. The molecules that are involved in PI3K-AKT signaling targeted by Compound I are depicted in a dark grey color.
Figure 15:
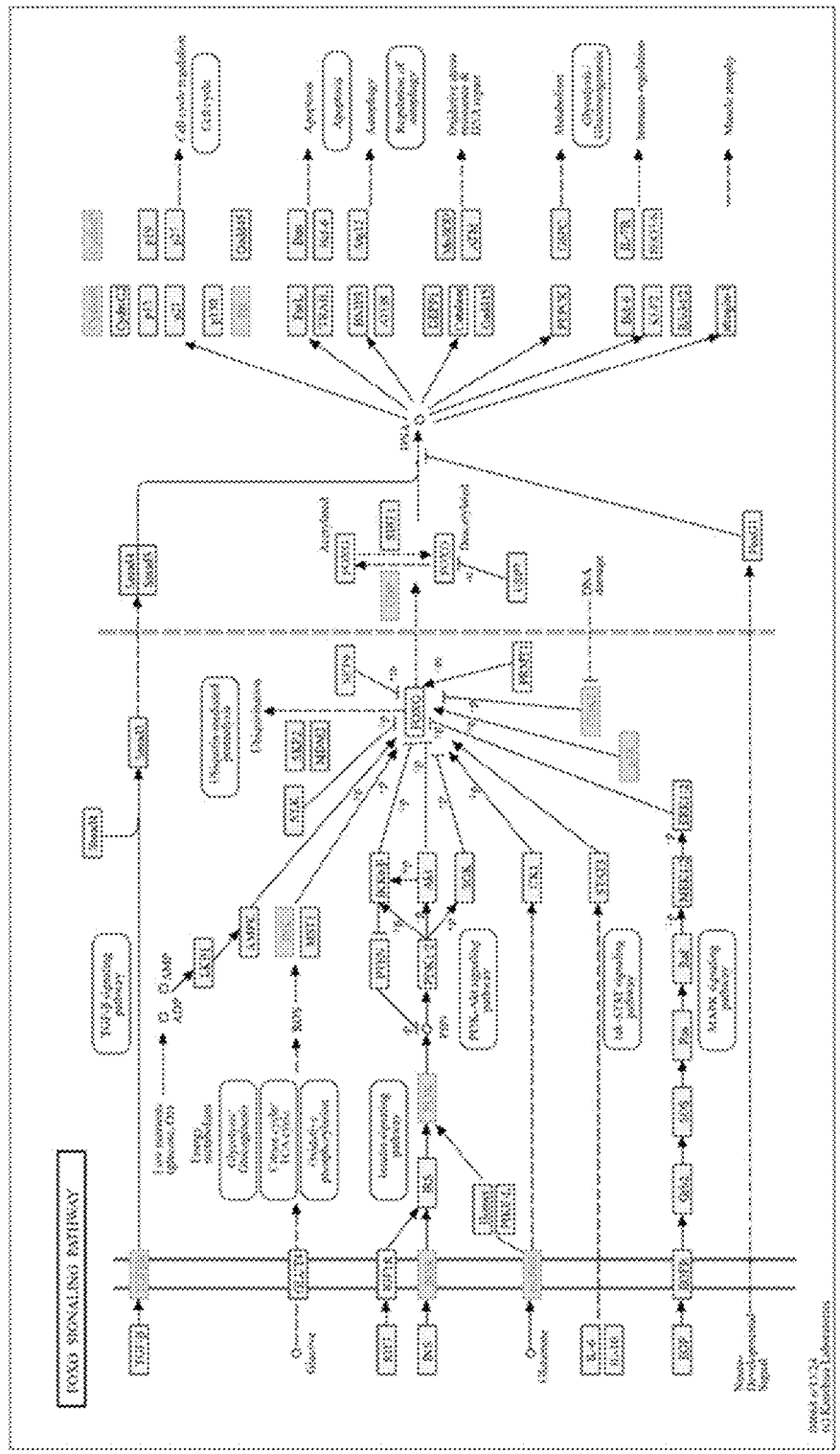
FIG. 15. Illustration of the pathways in FoxO signaling according to KEGG. The molecules that are involved in FoxO signaling targeted by Compound I are depicted in a dark grey color.
Figure 16:
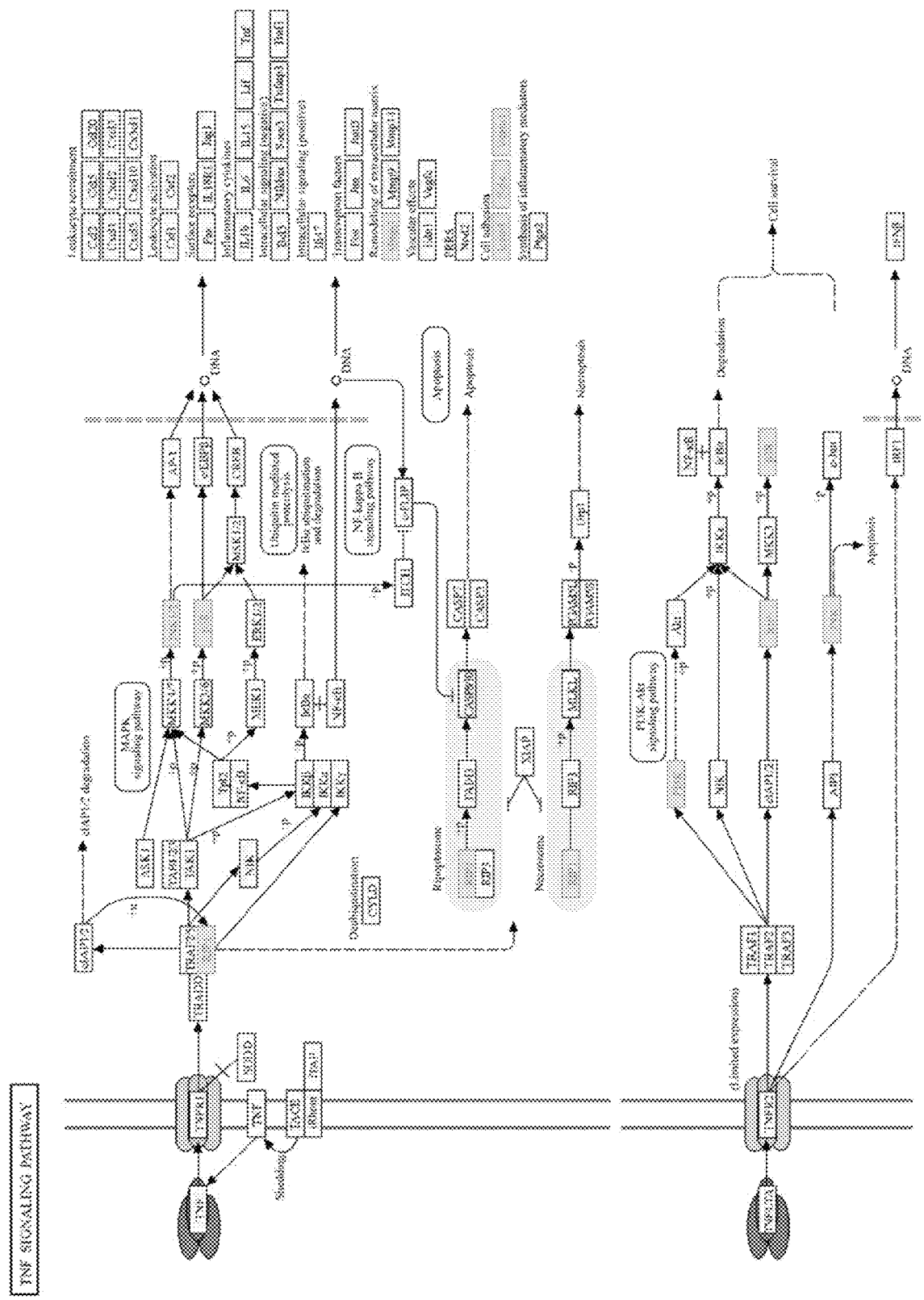
FIG. 16. Illustration of the pathways in TNF signaling according to KEGG. The molecules that are involved in TNF signaling targeted by Compound I are depicted in a dark grey color.

In silico mechanism:

SwissTargetPrediction KEGG tool was used to decode the molecular targets of Compound I, as shown in FIG. 10 and FIG. 11. Enriched KEGG pathways related to cancer were identified as targets of Compound I, including its effects on the cell cycle (FIG. 12), P53 signaling (FIG. 13), PI3K-AKT signaling (FIG. 14), FoxO signaling (FIG. 15), and TNF signaling (FIG. 16) using the WebGestalt tool as previously described (Kalamegam et al., 2020). The enrichment results for the top pathways related to cancer and inflammation affected by Compound I treatment are summarized in FIG. 10 (Table).

Compound I showed proper molecular parameters for drug candidates as predicted by in silico tools adopted from Swiss ADME (Daina, Michielin et al. 2017), a website sponsored by the Swiss Institute of Bioinformatics (SIB) and dedicated to support drug discovery researchers to evaluate their drug candidates (FIG. 17). For instance, Compound I has a molecular weight (MW) of 346.4, topological polar surface area (TPSA) of 83.98, and average (Consensus Log P) of 1.95. Compound I was also placed in the category (Soluble), which evaluates its probability of solubilizing in the biological conditions of the GI system. These parameters were reflected in it druggability evaluations (FIG. 18) as it was found aligned with commonly used parameters such as Lipinski, Ghose, Veber, Egan and Muegge rules. It had an excellent bioavailability score (0.55) and no PAINS alerts.

Compounds 1, 2, or 3 can be formulated as compositions will be generally administered in a pharmaceutically acceptable formulation which includes suitable excipients, elixirs, and the like (generally referred to as "pharmaceutically and physiologically acceptable carriers"), which are pharmaceutically acceptable and compatible with the active ingredients (compounds 1, 2, or 3 or salts or solvates thereof). Compounds 1, 2, or 3 may be present in the formulation as pharmaceutically acceptable salts (e.g. alkali metal salts such as sodium, potassium, calcium or lithium salts, ammonium, etc.) or as other complexes. Pharmaceutically acceptable formulations include solid, semi-solid, and liquid materials conventionally utilized to prepare solid, semi-solid and liquid dosage forms such as tablets, capsules, liquids, aerosolized dosage forms, and various injectable forms (e.g., forms for intravenous administration), etc. Suitable pharmaceutical carriers include but are not limited to inert solid diluents or fillers, sterile aqueous solutions and various organic solvents. Examples of solid carriers (diluents, excipients) include lactose, starch, conventional disintegrating agents, coatings, lactose, terra alba, sucrose, talc, gelatin, agar, pectin, acacia, magnesium stearate, stearic acid and lower alkyl ethers of cellulose. Examples of liquid carriers include but are not limited to various aqueous or oil based vehicles, saline, dextrose, glycerol, ethanol, isopropanol, phosphate buffer, syrup, peanut oil, olive oil, phospholipids, fatty acids, fatty acid amines, polyoxyethylene, isopropyl myristate, ethyl cocoate, octyl cocoate, polyoxyethylenated hydrogenated castor oil, paraffin, liquid paraffin, propylene glycol, celluloses, parabens, stearyl alcohol, polyethylene glycol, isopropyl myristate, phenoxyethanol, and the like, or combinations thereof. Water may be used as the carrier for the preparation of compositions which may also include conventional buffers and agents to render the composition isotonic. Oral dosage forms may include various thickeners, flavorings, diluents, emulsifiers, dispersing aids, binders, coatings and the like. The composition of the present disclosure may contain any such additional ingredients so as to provide the composition in a form suitable for the intended route of administration. In addition, the composition may contain minor amounts of auxiliary substances such as wetting or emulsifying agents, pH buffering agents, and the like. Similarly, the carrier or diluent may include any sustained release material known in the art, such as glycerol monostearate or glycerol distearate, alone or mixed with wax. Other potential additives and other materials (preferably those which are generally regarded as safe [GRAS]) include: colorants; flavorings; surfactants (TWEEN®, oleic acid, etc.); and solvents, stabilizers, binders or encapsulants (lactose, liposomes, etc.). Preservatives such as methyl paraben or benzalkium chloride may also be used. Depending on the formulation, it is expected that the active components (e.g. Compounds 1, 2, or 3) will be present at about 1% to about 99% of the composition and the vehicular "carrier" will constitute about 1% to about 99% of the composition. The pharmaceutical compositions of the present disclosure may include any suitable pharmaceutically acceptable additives or adjuncts to the extent that they do not hinder or interfere with the therapeutic effect(s) of the composition. Still other suitable formulations for use in the present disclosure can be found, for example in Remington's Pharmaceutical Sciences 22nd edition, Allen, Loyd V., Jr editor (September 2012); and Akers, Michael J. Sterile Drug Products: Formulation, Packaging, Manufacturing and Quality; publisher Informa Healthcare (2010).

The compositions (preparations) of the present disclosure are formulated for administration by any of the many suitable means which are known to those of skill in the art, including but not limited to: orally, by injection, rectally, by inhalation, intravaginally, intranasally, topically, as eye drops, via sprays, transdermally, sublingually, by rectal and buccal delivery, by inhalation of an aerosol, by microneedle delivery, etc. In some aspects, the mode of administration is preferably intravenous infusion.

The administration of the compound of the present disclosure may be intermittent, or at a gradual or continuous, constant or controlled rate (e.g. in a continuous IV infusion). In addition, the time of day and the number of times per day that the pharmaceutical formulation is administered vary and are best determined by a skilled practitioner such as a physician. Generally, the compounds are administered at least once a day, and may be administered e.g., 2, 3, 4, or more times per day. During a crisis or critical illness, administration may be more frequent or even continuous.

Administration of the compound by any means may be carried out as a single mode of therapy, or in conjunction with other therapies and treatment modalities, e.g., antibiotics, pain medication, hydroxyurea, vaccinations, blood transfusions, provision of supplemental oxygen, gene therapy, nitric oxide, drugs to boost fetal hemoglobin production, statins, etc. In addition, if disease sequalae includes other morbidities, e.g. a heart condition, then additional treatments for heart disease may be provided, including surgery. Other treatment options include various neutraceuticals, diet regimens, exercise, etc. "In conjunction with" refers to both administration of a separate preparation of the one or more additional agents, and to inclusion of the one or more additional agents in a composition of the present disclosure.

The subject to whom the composition is administered is generally a mammal, e.g., a human, but this is not always the case. Veterinary applications of this technology are also contemplated, e.g., for companion pets (cats, dogs, etc.), or for livestock and farm animals, for horses, and even for "wild" animals that have special value or that are under the care of a veterinarian, e.g., animals in preserves or zoos, injured animals that are being rehabilitated, etc.

ACKNOWLEDGMENT OF SPONSORED RESEARCH

This work was funded by the University of Jeddah, Jeddah, Saudi Arabia, under grant No. (UJ-23-RSP-7). The authors, therefore, thank the University of Jeddah for its technical and financial support.

REFERENCES

Alkhatabi H A, Zohny S F, Shait Mohammed M R, Choudhry H, Rehan M, Ahmad A, Ahmed F, Khan M I. Venetoclax-Resistant MV4-11 Leukemic Cells Activate PI3K/AKT Pathway for Metabolic Reprogramming and Redox Adaptation for Survival. Antioxidants (Basel). 2022 Feb. 25; 11 (3): 461. doi: 10.3390/antiox11030461.

Alkhatabi H A, Alqahtani W, Alsolami R, Elaimi A, Hazzazi M S, Almashjary M N, Alkhatabi H A, Alghuthami M E, Daous Y M, Yasin E B, Barefah A. Application of Newly Customized Myeloid NGS Panel in the Diagnosis of Myeloid Malignancies. Int J Gen Med. 2024 Jan. 6; 17:37-48. doi: 10.2147/IJGM.S437327. PMID: 38204493; PMCID: PMC10777859.

Daina A, Michielin O, Zoete V. SwissADME: a free web tool to evaluate pharmacokinetics, drug-likeness and medicinal chemistry friendliness of small molecules. Sci Rep. 2017 Mar. 3; 7:42717. doi: 10.1038/srep42717.

DiNardo C D, Cortes J E. New treatment for acute myelogenous leukemia. Expert Opin Pharmacother. 2015 January; 16 (1): 95-106. doi: 10.1517/14656566.2015.981527.

DiNardo C D, Erba H P, Freeman S D, Wei A H. Acute myeloid leukaemia. Lancet. 2023 Jun. 17; 401 (10393): 2073-2086. doi: 10.1016/S0140-6736 (23) 00108-3.

Elizarraras J M, Liao Y, Shi Z, Zhu Q, Pico A R, Zhang B. WebGestalt 2024: faster gene set analysis and new support for metabolomics and multi-omics. Nucleic Acids Res. 2024 May 29: gkae456. doi: 10.1093/nar/gkae456.

Haouas H. Angiogenesis and acute myeloid leukemia. Hematology. 2014 September; 19 (6): 311-23. doi: 10.1179/1607845413Y.0000000139.

Kalamegam G, Alfakeeh S M, Bahmaid A O, AlHuwait E A, Gari M A, Abbas M M, Ahmed F, Abu-Elmagd M, Pushparaj P N. In vitro Evaluation of the Anti-inflammatory Effects of Thymoquinone in Osteoarthritis and in silico Analysis of Inter-Related Pathways in Age-Related Degenerative Diseases. Front Cell Dev Biol. 2020 Jul. 23; 8:646. doi: 10.3389/fcell.2020.00646.

Kanehisa M, Goto S. KEGG: kyoto encyclopedia of genes and genomes. Nucleic Acids Res. 2000 Jan. 1; 28 (1): 27-30. doi: 10.1093/nar/28.1.27.

Koklu H, Tufan A, Erkul Y, Akyurek N, Civelek R. Secondary acute myeloid leukemia arising early after cyclophosphamide treatment. Int J Clin Pharm. 2015 April; 37 (2): 289-91. doi: 10.1007/s11096-015-0069-4. Epub 2015 Jan. 23. PMID: 25612567.

Liang Y, Wang S, Liu J. Overexpression of Tumor Protein p53-regulated Apoptosis-inducing Protein 1 Regulates Proliferation and Apoptosis of Breast Cancer Cells through the PI3K/Akt Pathway. J Breast Cancer. 2019 June; 22 (2): 172-184. doi: 10.4048/jbc.2019.22.e21.

Lu J, Zhang Y, Wang S, Bi Y, Huang T, Luo X, Cai Y D. Analysis of Four Types of Leukemia Using Gene Ontology Term and Kyoto Encyclopedia of Genes and Genomes Pathway Enrichment Scores. Comb Chem High Throughput Screen. 2020; 23 (4): 295-303. doi: 10.2174/1386207322666181231151900.

Medinger M, Heim D, Halter J P, Lengerke C, Passweg J R. Diagnostik und Therapie der Akuten Myeloischen Leukämie [Diagnosis and Therapy of Acute Myeloid Leukemia]. Ther Umsch. 2019; 76 (9): 481-486. German. doi: 10.1024/0040-5930/a001126.

PubChem [Internet]. Bethesda (MD): National Library of Medicine (US), National Center for Biotechnology Information; 2004-. PubChem Bioassay Record for AID 1937, Protocol for Protein Binding Rapid Equilibrium Dialysis (RED) Assay in Mouse Plasma, Source: Burnham Center for Chemical Genomics; [cited 2024 Jul. 3]. Available from the https page pubchem.ncbi.nlm.nih.gov/bioassay/1937.

Subramanian A, Kuehn H, Gould J, Tamayo P, Mesirov J P. GSEA-P: a desktop application for Gene Set Enrichment Analysis. Bioinformatics. 2007 Dec. 1; 23 (23): 3251-3. doi: 10.1093/bioinformatics/btm369. Epub 2007 Jul. 20.

Vakiti A, Reynolds S B, Mewawalla P. Acute Myeloid Leukemia. 2024 Apr. 27. In: StatPearls [Internet]. Treasure Island (FL): StatPearls Publishing; 2024 January.

Zhang X, Tang N, Hadden T J, Rishi A K. Akt, FoxO and regulation of apoptosis. Biochim Biophys Acta. 2011 November; 1813 (11): 1978-86. doi: 10.1016/j.bbamcr.2011.03.010. Epub 2011 Mar. 31.

We claim:

1. A method for treating acute myeloid leukemia by administering to a subject in need thereof an effective amount of a compound or pharmaceutically accepted salt or solvate thereof, selected from the group consisting of

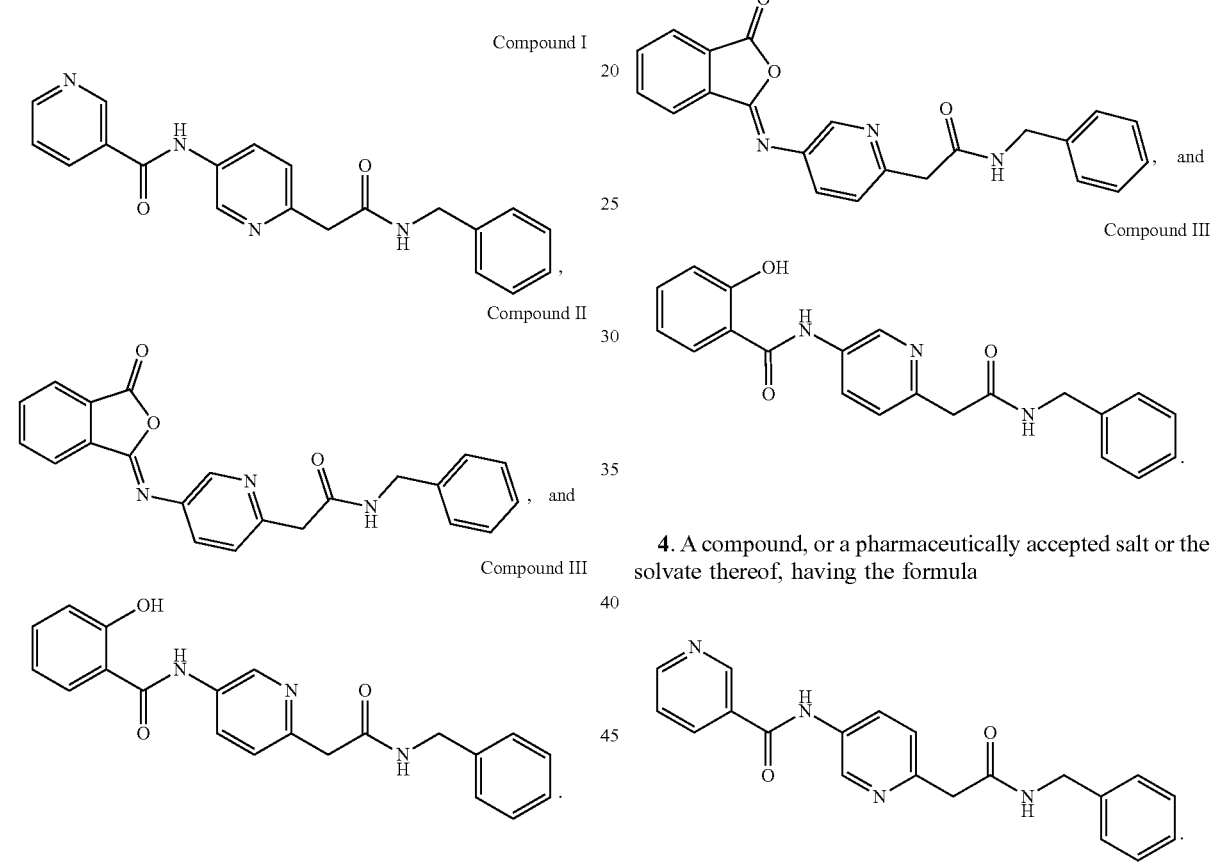

2. The method of claim 1 wherein said therapeutically effective amount of Compound 1 is sufficient to inhibit leukemic cell growth and/or proliferation.

3. A compound, or a pharmaceutically accepted salt or the solvate thereof, selected from the group consisting of 4. A compound, or a pharmaceutically accepted salt or the solvate thereof, having the formula

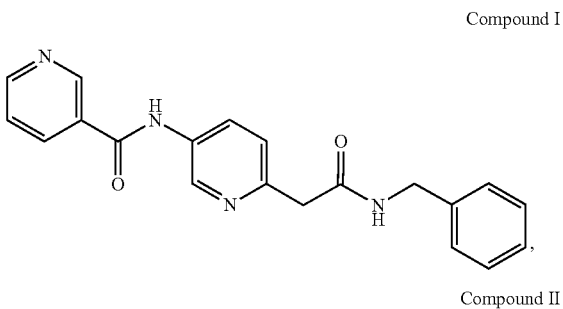

* * * * *